US008470263B2

(12) United States Patent
Shih et al.

(10) Patent No.: US 8,470,263 B2
(45) Date of Patent: Jun. 25, 2013

(54) MICROFLUIDIC DEVICE

(75) Inventors: Chih-Hsin Shih, Taichung (TW); Hou-Jin Wu, Taichung (TW); Chih-Huong Yeh, Taichung (TW); Wen-Hao Chen, Taichung (TW); Kang-Yang Fan, New Taipei (TW); Jin-Pin Hung, Taipei (TW)

(73) Assignee: AMPOC Far-East Co., Ltd., Taipei (TW)

( * ) Notice: Subject to any disclaimer, the term of this patent is extended or adjusted under 35 U.S.C. 154(b) by 186 days.

(21) Appl. No.: 13/071,578

(22) Filed: Mar. 25, 2011

(65) Prior Publication Data

US 2012/0241035 A1 Sep. 27, 2012

(51) Int. Cl.
*G01N 15/06* (2006.01)
*G01N 33/00* (2006.01)
*G01N 33/48* (2006.01)

(52) U.S. Cl.
USPC .......... 422/503

(58) Field of Classification Search
USPC .......... 422/68.1, 81, 82, 502, 503, 506, 422/507, 509; 436/43, 180
See application file for complete search history.

(56) References Cited

U.S. PATENT DOCUMENTS 6,143,248 A 11/2000 Kellogg et al.

OTHER PUBLICATIONS

Elsevier Science B.V., Sensors and Actuators B 75, "Hydrophibic Valves of Plasma Deposited Octafluorocyclobutane in DRIE Channels", Helene Andersson, et al., 2001, pp. 136-141.

Elsevier Inc., Journal of Collid and Interface Science 306, "How the Capillary Burst Microvalve Works", Hansang Cho, et al., 2006, pp. 379-385.

Elsevier Science B.V., Sensors and Actuators A 108, "Passive Valves Based on Hydrophobic Microfluidics", Yanying Feng, et al., 2003, pp. 138-143.

Institute of Physics Publishing, Journal of Micromechanics and Microengineering, "A Review of Microvalves", Kwang W. Oh, et al., 2006, pp. R13-R39.

*Primary Examiner* — Brian J Sines
(74) *Attorney, Agent, or Firm* — Fishman & Associates, LLC.

(57) ABSTRACT

A microfluidic device has a body, multiple channels, multiple reservoirs and multiple capillary valves. The reservoirs are formed on the body. Each channel is formed on the body and connects to a corresponding reservoir. The channels include a main channel and at least one branch channel. The main channel is formed on the top of the body and extends in a direction from the center to a circumference of the body. Each capillary valve is mounted on a corresponding channel and at a distance substantially close to the center of the body so differences between the burst frequencies of the capillary valves are increased. The microfluidic device has an excellent flow control on sequentially releasing fluid through distinct burst frequencies of microcapillary valves.

18 Claims, 8 Drawing Sheets

MICROFLUIDIC DEVICE

BACKGROUND OF THE INVENTION

1. Field of the Invention

The present invention relates to a microfluidic device, and more particularly to a microfluidic device motivated by centrifugal force that has an improved flow control of fluid on its flowing into channels by adjusting burst frequencies of capillary valves.

2. Description of the Prior Arts

Due to developments in medicine, pharmacy, biotechnology and environmental monitoring, overwhelming chemical analysis and related devices and technicians are required. However, the general public needs a more convenient and simpler analytical process without being limited by technical knowledge, devices and occasions.

With progresses of microelectronic techniques and semiconductors, great efforts have been devoted to the development of efficient, sensitive, precise and miniature automatic detection techniques in the field of biological analysis and biomedical diagnostics. The concept of Micro Total Analysis Systems (μTAS) was proposed in the early 1990s. Merely one μTAS is capable of including sample preparation, chemical reaction, separation and purification of, and detection and analysis of analyte as a complete chemical analytic process. Thus, μTAS satisfies the need for a more convenient and simpler analytical process.

Miniature of μTAS is beneficial in that it is easy to carry. Use of microelectronic components in μTAS lowers electricity consumption and reduces cost. Moreover, μTAS requires smaller amounts of samples or reagents, resulting in decrease of expenses on reagents. Furthermore, during procedures of an automatic chemical process, flow rate, amount of materials and sequence of reactions in each procedure profoundly affect the results of the analysis. μTAS is regarded as a minimized batch chemical process. A major focus of studies in μTAS is microfluidic technique. The microfluidic techniques encompass various fluidic functions, such as valving, mixing, metering, splitting and separation.

Microfluid is driven by various methods, including mechanical micropumps and non-mechanical micropumps. The former includes peristaltic pump, ultrasonic pump and centrifugal pump. The latter includes pumping by electrical, magnetic, and gravity forces. In the case of the centrifugal pump, it is used in disc type microanalytical system, also called microfluidic disc system. Microfluidic disc system motivates fluid flow by centrifugal force and controls fluid flow by using passive capillary valve. The underlying mechanism of passive capillary valve is that capillary pressure difference or Laplace pressure difference prevents fluid flow. Therefore, fluid flow can be regulated by manipulating the balance between centrifugal force and capillary pressure. The critical rotational frequency, corresponding to the centrifugal force which overcomes the capillary pressure, is called burst frequency.

As for capillary valves in microfluidic system, currently a lot of related techniques have been published. U.S. Pat. No. 6,143,248 discloses that capillary pressure is associated with the arrangement, geometry and surface characters of capillary valves and reservoirs, and quantitative transferring of fluid is achieved under a related principle. In 2001, Anderson et al. modifies a portion of a microchannel by inductively-coupled plasma (ICP) with hydrophobic materials to form a hydrophobic surface on a portion of the microchannel. The change of the surface property produces a valving effect called hydrophobic valve. In 2003, Feng et al. disclose that hydrophobic valve can also be made by self-assembled monolayers (SAMs) by changing the geometry of channel to produce valve effect. In 2006, Cho et al. adopt annular channels and rectangular channels in capillary valving, propose a model of capillary valves with different angles of opening (60°, 90° and 120°) and verify predicted burst frequencies with experimental results. In 2006, Kwang et al. suggest that capillary valving is useful for microfluidic control process and further illustrate that fluid flow can be controlled by capillary valve through the changes of geometry and surface property of microchannels.

However, the aforesaid references only propose control of fluid flow with changes in geometry and surface modification and how to predict burst frequency. None of them reveals the relationship between positions, arrangement or orientation of capillary valves in the microfluidic system, especially the significance of positions proximal to the center of the microfluidic disc to fluid flow control. Moreover, almost all current microchannels are arranged at positions with a larger radial on the microfluidic disc because more microchannels can be implemented. Under those designs, the burst frequencies for the valves are usually lower than 2000 RPM. Since the burst frequencies of the capillary valves at positions with various radial distances are limited to lower than 2000 RPM, they tend to overlap each other. Therefore, current techniques of burst valves have disadvantages of unable to effectively release fluid in correct sequence.

To overcome the shortcomings, the present invention provides a microflluidic device to mitigate or obviate the aforementioned problems.

SUMMARY OF THE INVENTION

A microfluidic device in accordance with the present invention comprises a body, multiple channels, multiple reservoirs, multiple capillary valves and a cover.

The body is in a shape of annular disk and has a top, a center and a circumference. The reservoirs are formed on the top of the body. Each channel is formed on the top of the body and connects to a corresponding reservoir. The channels include a main channel and at least one branch channel. The main channel is formed on the top of the body and extends in a direction from the center to the circumference of the body. Each capillary valve is mounted on a corresponding channel and at a distance substantially close to the center of the body so as to increase differences between the burst frequencies of the capillary valves. The cover is mounted on the top of the body and has multiple apertures corresponding to the reservoirs.

Preferably, the distance of each of the capillary valves to the center of the body is lesser than 4 cm.

Preferably, the main channel has a first end and a second end. The second end is opposite the first end and between the first end and the circumference of the body. The multiple branch channels connect to the main channel. The multiple reservoirs include a first reservoir and a second reservoir. The first reservoir connects to the first end of the main channel. The second reservoir is formed between the first reservoir and the circumference of the body and connects to a branch channel and communicates with the main channel. The capillary valves include a first capillary valve and a second capillary valve. The first capillary valve is mounted between the first reservoir and the main channel. The second capillary valve is mounted between and connects the branch channel and the second reservoir.

Preferably, a width of the first capillary valve (at the inner radius) is smaller than a width of the second capillary valve (at the outer radius), whereby difference between the burst frequencies thereof is increased.

Preferably, the arrangement has multiple reservoirs including a third reservoir, a fourth reservoir and a fifth reservoir. The fifth reservoir connects to the second end of the main channel. The third reservoir is mounted between the second reservoir and the fourth reservoir and connects to the main channel through a corresponding branch channel. The fourth reservoir is mounted between the third reservoir and the fifth reservoir and connects to the main channel through another corresponding branch channel. The multiple capillary valves further include a third capillary valve and a fourth capillary valve. The third capillary valve is mounted on the corresponding branch channel and between the third reservoir and the main channel. The fourth capillary valve is mounted on the corresponding branch channel between the fourth reservoir and the main channel.

Preferably, a width of the second capillary valve is smaller than a width of the third capillary valve, whereby difference between the burst frequencies thereof is increased.

Preferably, a width of the third capillary valve is smaller than a width of the fourth capillary valve, whereby difference between the burst frequencies thereof is increased.

Preferably, the first capillary valve has a hydrophobically modified inner surface.

Preferably, each of the first capillary valve, second capillary valve, the third capillary valve except the fourth capillary valve (the valve near the rim) has a hydrophobically modified inner surface.

More preferably, the microfluidic device in accordance with the present invention includes an additional branch channel. The additional branch channel is mounted between the main channel and the first reservoir and has a distal end and a proximal end. The distal end connects to the first capillary valve and the main channel. The proximal end connects the distal end and the main channel and is not parallel to the main channel. More preferably, the proximal end of the additional branch channel is vertical to the centrifugal direction.

Preferably, the fifth reservoir is a detection chamber or a waste chamber.

Preferably, the cover is prepared from the materials selected from the group consisting of: polycarbonate, poly (methyl methacrylate), polystyrene and cyclic olefin copolymer.

Based on the aforesaid descriptions, the radial distances of the capillary valves in accordance with the present invention are smaller than 4 cm. As compared to the conventional microfluidic techniques, the capillary valves are closer to the center of the body. The microfluidic device in accordance with the present invention can be beneficial in sequentially releasing fluid. By adjusting the valve width, orientation and surface modification of the capillary valves, the excellent effect of sequential releasing of fluid of the microfluidic device according to the present invention is useful for various applications on chemical analytical processes.

Other objectives, advantages and novel features of the invention will become more apparent from the following detailed description when taken in conjunction with the accompanying drawings.

DETAILED DESCRIPTION OF THE PREFERRED EMBODIMENTS

The present invention is based on centrifugation as the main driving force for actuating low volume fluid. When fluid flows in microchannels to a capillary valve, the capillary pressure difference caused by surface tension and the change of interfacial free energy among liquid, gas and solid phases, results in change of its flowing behavior and stop the flow. Therefore, a passive capillary valving can be modulated by its arrangement, geometry and surface modification.

Figure 1:
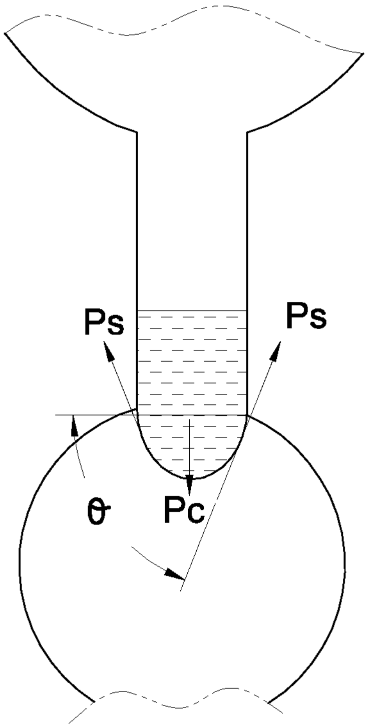
FIG. 1 is a scheme illustrating capillary pressure and centrifugal force in a capillary valve.

With reference to FIG. 1, a capillary valve in accordance with the present invention has a burst frequency determined by balance of pressure induced by centrifugal force (ΔPc) and capillary pressure (ΔPs). When capillary pressure is constant, the pressure induced by centrifugal force becomes the critical factor that affects burst frequency. The pressure induced by centrifugal force is determined by the following equation:

$$\Delta P_c=\rho\cdot\omega^2\cdot\Delta R\cdot\overline{R}.$$

The capillary pressure is determined by the following equation:

$$\Delta P_s=\frac{C\gamma\sin\theta}{A},$$

wherein ρ is density of fluid, ω is angular frequency, ΔR is difference between radial distance from the center of disk to surface of fluid in reservoir and to surface of fluid in capillary valve, $\overline{R}$ is an average of radial distance of surface of fluid in reservoir and that of capillary valve, C is wetting circumference, γ is surface tension, θ is contact angle of the fluid to the surface of the compact disk, A is cross-sectional area of the channel. When centrifugal force and capillary pressure are balanced, the burst frequency is calculated by the following equation:

$$\omega=\sqrt{\frac{C\gamma\sin\theta}{A\cdot\rho\cdot\Delta R\cdot\overline{R}}}$$

By changing rotational frequency of platform, pressure induced by centrifugal force at reservoir located at different radial distances from center of microfluidic disk can be modulated as desired. Once rotational frequency of the platform is higher than burst frequency of a predetermined reservoir, fluid sample in the predetermined reservoir is actuated by centrifugal force and overcomes capillary pressure of capillary valve so as to flow past the capillary valve.

Figure 2:
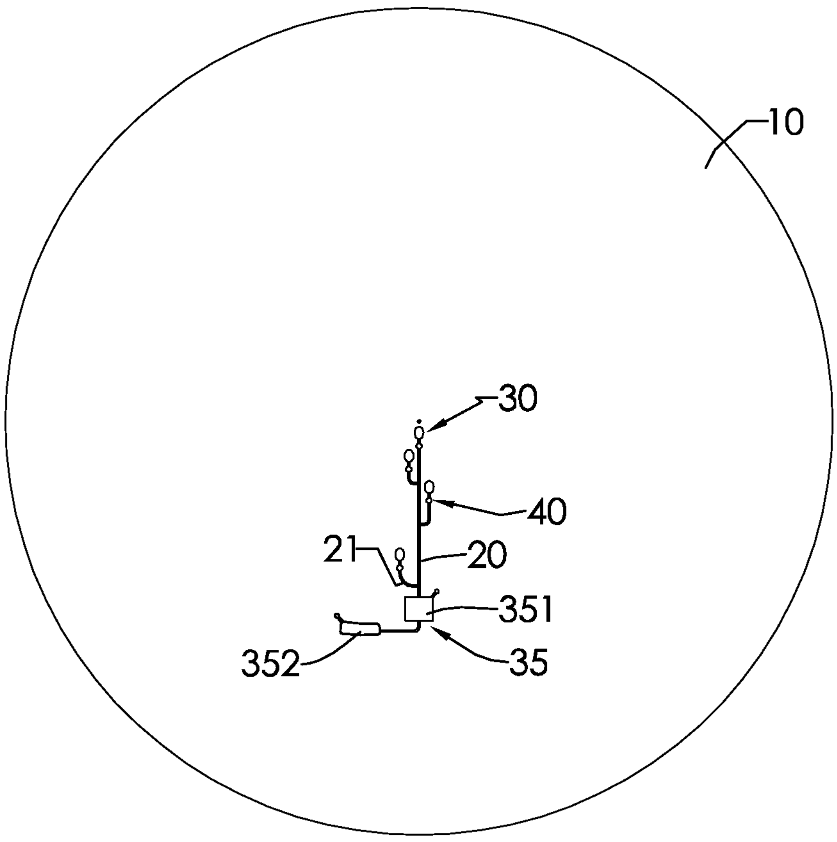
FIG. 2 is a top view of a body of a microfluid device in accordance with the present invention.
Figure 3:
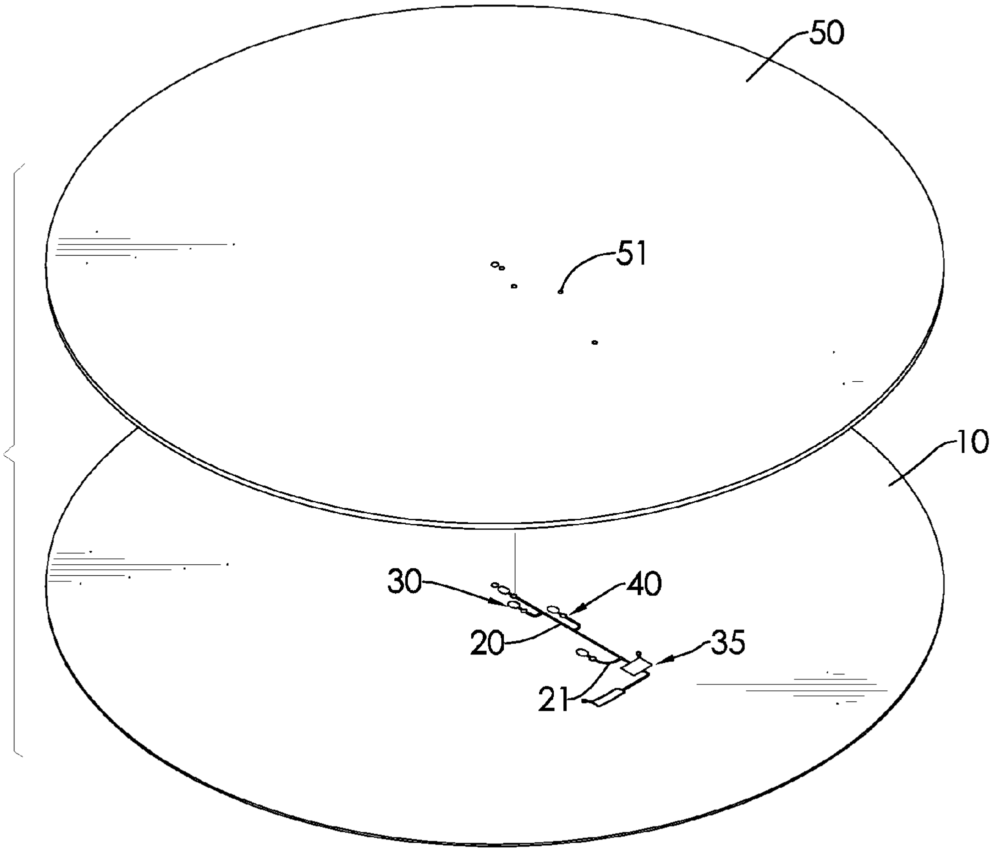
FIG. 3 is a perspective exploded view of a body of a microfluid device in accordance with the present invention.

With reference to FIG. 2 and FIG. 3, the present invention provides a microfluidic device comprises a body 10, a main channel 20, multiple branch channels 21, multiple reservoirs 30, multiple capillary valves 40 and a cover 50.

The body 10 is in a shape of annular disk and prepared from materials selected from the group consisting of: polycarbonate (PC), poly(methyl methacrylate) (PMMA), polystyrene (PS), cyclic olefin copolymer (COC) and their substitutive materials. The body 20 has a top, a center and a circumference.

The main channel 20 and each branch channel 21 are formed on the top of the body 10. The main channel 20 extends in a direction from the center of the body 10 toward the circumference of the body 10 and has a first end and a second end. The second end is opposite to the first end and located between the first end and the circumference of the body 10. Each branch channel 21 connects to and communicates with the main channel 20.

Each reservoir 30 is formed on the top of the body 10. The number of the reservoirs 30 is determined by requirements of analysis. In a preferred embodiment of the present invention, with reference to FIG. 4, the microfluidic device in accordance with the present invention has five reservoirs including a first reservoir 31, a second reservoir 32, a third reservoir 33, a fourth reservoir 34 and a fifth reservoir 35. The first reservoir 31 connects to the first end of the main channel 20. Radial distance of the first reservoir 31 is shortest among all reservoirs. The first reservoir 31 is closest to the center of the body 10 among the reservoirs. “Radial distance” as used hereby, refers to the distance from the center of the body 10 to a referred subject matter. The fifth reservoir 35 connects to and communicates with the second end of the main channel 20. The second reservoir 32, the third reservoir 33 and the fourth reservoir 34 are located between the first reservoir 31 and the fifth reservoir 35 and respectively connect to and communicate with corresponding branch channels 21. With further reference to FIG. 2, the fifth reservoir 35 includes a mixture chamber 351 and waste chamber 352. The mixture chamber 351 connects to the second end of the main channel 20 to collect fluid flowing from main channel 20. The waste chamber 352 connects to the mixture chamber 351 to collect fluid flowing from the mixture chamber 352.

The main channel 20, the branch channel 21 and the reservoirs 31, 32, 33, 34, 35 are formed on the top of the body 10 by machining, molding or photolithography and their substitutive processes.

Each capillary valve 40 is mounted on a corresponding main channel 20 or a corresponding branch channel 21. The number and the arrangement of capillary valves are determined by the requirements of analysis or manufacture. In a preferred embodiment in accordance with the present invention, with further reference to FIG. 4, the microfluidic device has four capillary valves 40 including a first capillary valve 41, a second capillary valve 42, a third capillary valve 43 and a fourth capillary valve 44. The first capillary valve 41 is mounted on and communicates with the main channel 20. The second capillary valve 42, the third capillary valve 43 and the fourth capillary valve 44 are respectively mounted on and communicates with corresponding branch channels 21. By changing the geometry and modifying inner surfaces of the first capillary valve 41, the second capillary valve 42, the third capillary valve 43 and the fourth capillary valve 44, a resistance to flow of fluid is produced. Since most of the liquid we are dealing with is aqueous solution, the inner surface of the first, second, and third capillary valves 41, 42, 43 should be hydrophobic and the no hydrophobic treatment should be placed on fourth (or the last) valve 44 so that the range of the burst frequency can be enlarged. In addition, the width of valve should be increasing from the first (inner) valve 41 to the fourth (outer) valve 44 with the inner valve has the shortest width.

Figure 4:
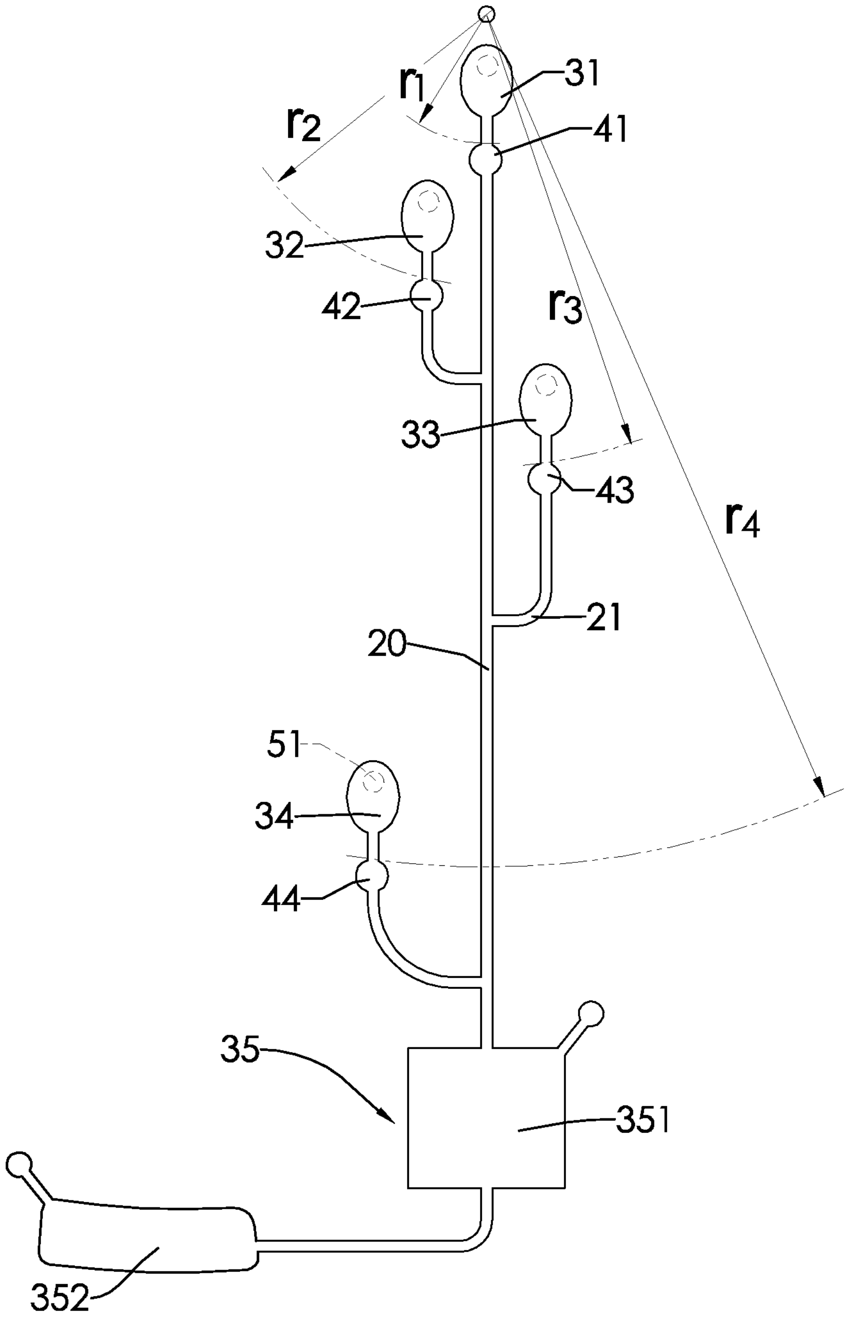
FIG. 4 is a top view of combination of the main channel, branch channels and reservoirs in FIG. 3.

With further reference to FIG. 4, the radial distances of the first capillary valve 41, the second capillary valve 42, the third capillary valve 43 and the fourth capillary valve 44 respectively are $r_1$ $r_2$ $r_3$ and $r_4$. In a preferred embodiment, $r_1$ $r_2$ $r_3$ and $r_4$ are shorter than 4 cm.

With reference to FIG. 3, the cover 50 is mounted on the top of the body 10 and has multiple apertures 51. The apertures 51 respectively correspond to the first reservoir 31, the second reservoir 32, the third reservoir 33 and the fourth reservoir 34. The cover 51 is prepared from materials selected from the group consisting of: polycarbonate, poly(methyl methacrylate, polystyrene, cyclic olefin copolymer and their substitutive substances.

Figure 7:
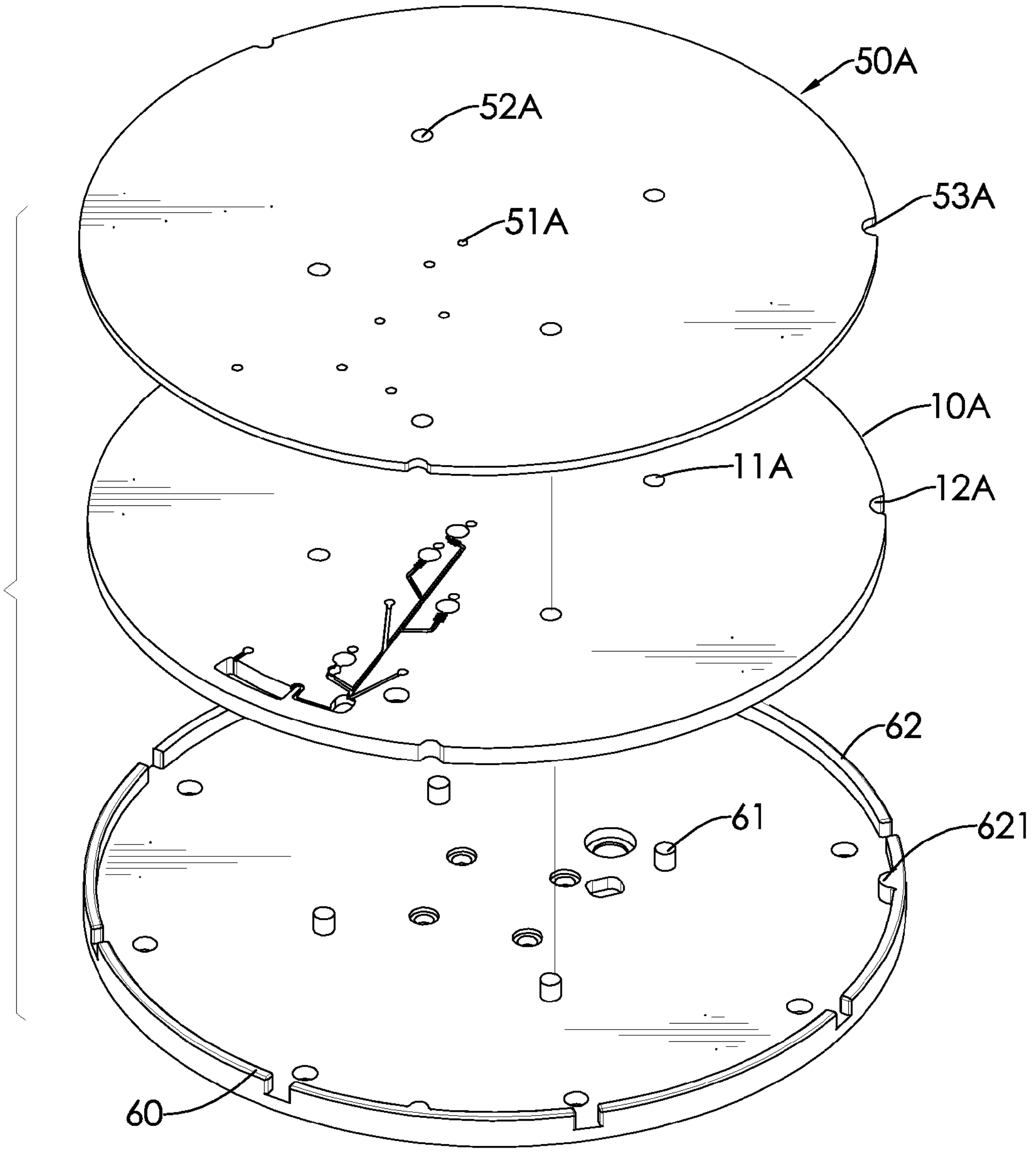
FIG. 7 is a perspective exploded view of a microfluidic device in accordance with the present invention mounted on a rotation platform.

In another preferred embodiment, as shown in FIG. 7, a microfluidic device in accordance with the present invention is adapted to be mounted on a rotation platform 60. The rotation platform 60 has multiple posts 61 and a flange 62. The flange 62 has multiple protrusions 621 extending toward center of the rotation platform 60. The body 10A further has multiple positioning apertures 11A and multiple notches 12A. The positioning apertures 11A respectively penetrate through the top and the bottom of the body 10A, and correspond to and mounted around the posts 61. The notches 12A respectively form on an edge of the body, and correspond to and engage with the protrusions 621. The cover 50A further has multiple positioning holes 52A and multiple recesses 53A. The positioning holes 52A respectively penetrate through a top and a bottom of the cover 50A, correspond to and mounted around the posts 61. The recesses 53A respectively form on a rim of the cover 50A, and correspond to and engage with the protrusions 621 of the flange 62 of the rotation platform 60. Based on the structure, when the rotation platform 60 rotates, the body 10A and the cover 50A can be steadily mounted on the rotation platform 60 and conveniently aligned with each other through engagement among the protrusions 621, the notches 12A and the recesses 53A and among the posts 61, the positioning apertures 11A and the positioning holes 52A.

EXAMPLES

Figure 5:
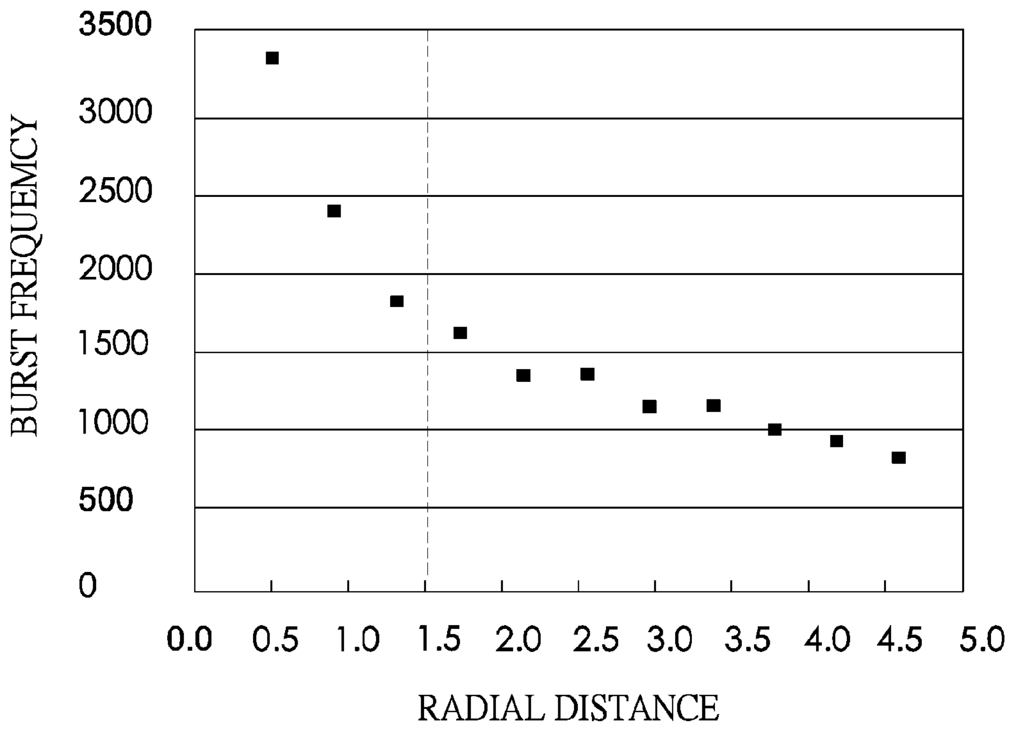
FIG. 5 is a scheme illustrating relationship between radial distances and burst frequencies of capillary valves.

1. Evaluating Relationship Between Radial Distance and Burst Frequency of a Capillary Valve:

One of the capillary valves 40 is formed at a radial distance of 0.5 cm and others are formed at an interval of 0.4 cm on the body 10. A valve width of each capillary valve 40 is 200 μm. The burst frequency of each capillary valve is determined. The relationship between radial distance and burst frequency of the capillary valve is shown in FIG. 5. Within a range of shorter radial distance between 0 and 1.5 cm, burst frequency of each capillary valve 40 drastically differs with radial distance. While within a range of larger radial distance between 2.0 and 4.5 cm, burst frequencies of capillary valves 40 differ little from each other and even overlap.

2. Comparing Burst Frequencies of Capillary Valves with Different Radial Distances:

Table 1 shows the radial distances and the valve widths of the first capillary valve 41, the second capillary valve 42, the third capillary valve 43 and the fourth capillary valve 44. The depths of the main channel 20 and branch channel 21 are all 200 μm. Inner surfaces of the capillary valves 41, 42, 43, 44 are modified by hydrophobic reagent and then are injected with 1.0 to 1.4 μl of liquid through apertures 51 into the corresponding reservoirs 31, 32, 33, 34. When the microfluidic device rotates, the rotational frequency starts at 500 RPM with an angular acceleratory rate of 100 RPM/second, followed by an increase of 50 RPM per 30 seconds at an angular acceleratory rate of 1000 RPM/second. Once liquid bursts into the capillary valves 41, 42, 43, 44 and flows in the channels 20, 21, the detected rotation rate is determined as the burst frequency of the said capillary valve. Comparing the design disclosed in the present invention (with valve positioned close to the center) and the conventional valve design (with valve positioned away from the center), as shown in Table 1, for similar design of valving structure, the burst frequency of the first capillary valve 41 is increased about 2.5 times and the difference of the burst frequency between first capillary valve 41 and the second capillary valve 42 is increased 4 times. Similar results are observed from the rest of the capillary valves 42, 43, 44, indicating that the burst frequency of a capillary valve at a smaller radial distance drastically increases comparing to that at a greater radial distance.

| | Conventional Design | | The design disclosed in this patent | |
|---|---|---|---|---|
| | Valve Radius/ Channel width | Burst frequency | Valve Radius/ Channel width | Burst frequency |
| first valve | 2.30 cm/100 μm | 1651 | 0.5 cm/100 μm | 4242 |
| second valve | 2.60 cm/200 μm | 1146 | 1.05 cm/200 μm | 2213 |
| third valve | 3.30 cm/250 μm | 700 | 1.75 cm/250 μm | 1300 |
| fourth valve | 4.85 cm/450 μm | 458 | 3.30 cm/450 μm | 750 |

For capillary valves of the conventional microfluidic device, their radial distances are usually designed between 1.5 cm to 6 cm. The reason for that is because the discs are manufactured through injection molding and center was used as the injection point and needs to be removed (such as CD manufacturing) or because the center is usually used as the fixation point to mount the disc to a rotating axel. However, the variation of centrifugal forces differs little at positions with larger radial distances. For example, the ratio of centrifugal force between the capillary valves of a radial distance of 4 cm and 5 cm is 4:5. Due to little variation between them, when fluid in the capillary valve of a radial distance of 5 cm bursts out, fluid in the capillary valve of a radial distance of 4 cm might also burst out. However, with the same interval of 1 cm, the ratio of centrifugal force between the capillary valves of a radial distance of 1 cm and 2 cm is 1:2. When fluid in the capillary valve of a radial distance of 2 cm bursts out, fluid in the capillary valve of a radial distance of 1 cm may not burst out. Therefore, for sequentially releasing fluid from reservoirs through the capillary valves into channels, the differences of the burst frequencies among the capillary valves should be large enough.

Figure 6A:
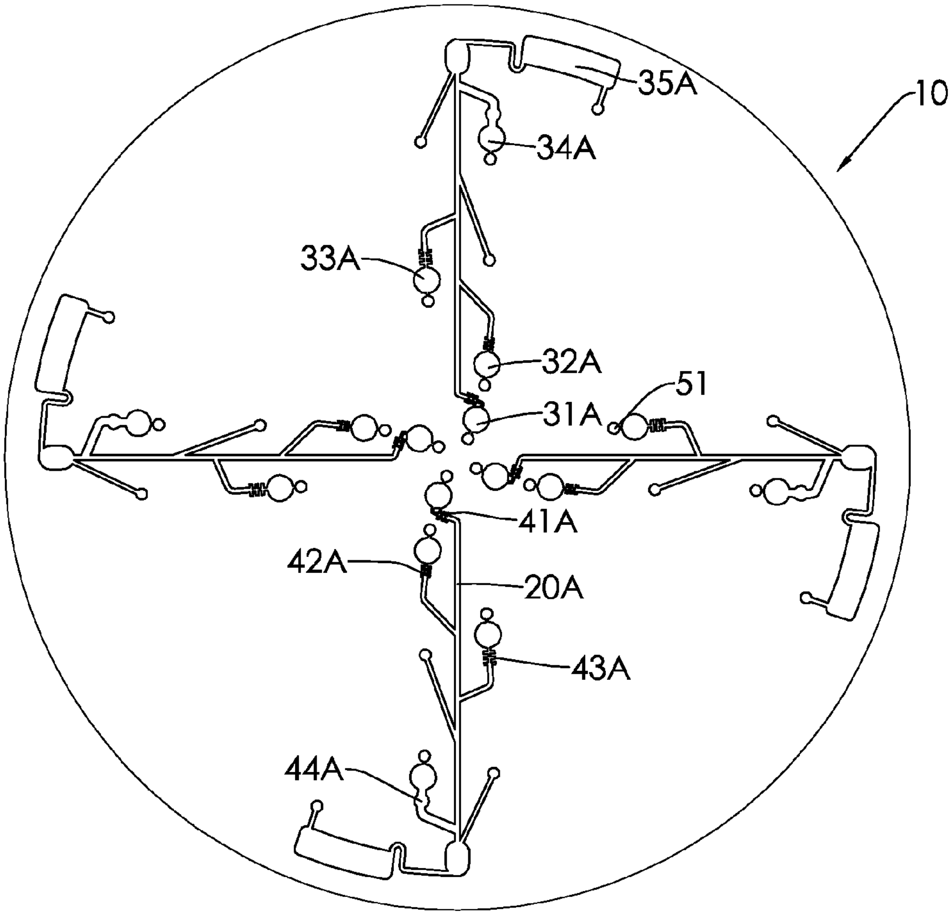
FIG. 6A is a top view of a second embodiment of the body of the microfluidic device in accordance with the present invention.
Figure 6B:
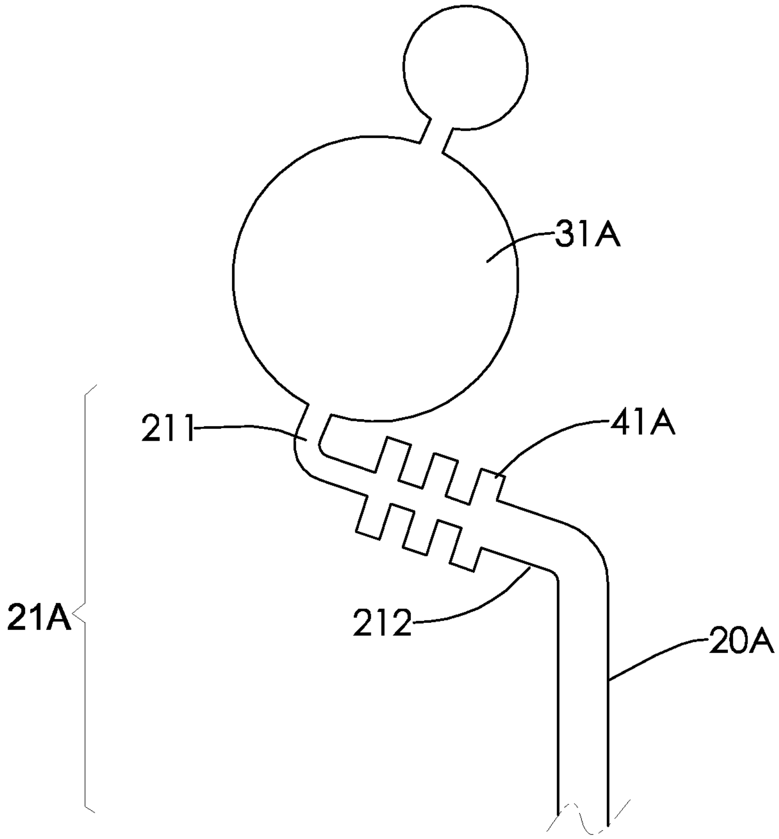
FIG. 6B is an enlarged top view of a portion of microfluidic device in FIG. 6A.

3. Evaluating the Relationship Among Valve Width, Orientation and Properties of the Inner Surface of the Capillary Valves and Sequential Release of Fluid:

With reference to FIGS. 6A and 6B, a preferred embodiment of a microfluidic device in accordance with the present invention is implemented, wherein an additional branch channel 21A is mounted between the main channel 20A and the first reservoir 31A and has a distal section 211 and a proximal section 212. The distal section connects 211 to the first capillary valve 41A. The proximal section 212 connects the distal section and the main channel 20A. The proximal section is not parallel to the main channel 20A. More particularly, the proximal section is vertical to the main channel 20A (centrifugal direction). The first capillary valve 41A is mounted between the proximal section 212 and the distal section 211. Therefore, the burst frequency of the first capillary valve 41A is further increased.

As shown in FIG. 6 and Table 1, the valve width of the first capillary valve 41A is smallest among all capillary valves 41A, 42A, 43A, 44A, and the valve width of the second capillary valve 42A is wider than the width of the first capillary valve 41A and so as to the third capillary valve 43A and the fourth capillary valve 44A. The fourth capillary valve 44A, the farthest from center of the body 10A has a widest valve width among all capillary valves 41A, 42A, 43A, 44A, The wider the valve width is, the lower burst frequency of the valve acquires. Through appropriate adjustment of valve width of the capillary valves 41A, 42A, 43A, 44A, intervals of burst frequency between capillary valves can be largely increased.

According to the above examples, the difference between two adjacent capillary valves decreases with the radial distance. Therefore, for aqueous solution, by hydrophobically modifying the inner surfaces of the capillary valves 41A, 42A, 43A closer to the center of the body 10A except for the capillary valve far from the center of the body 10A, the difference of the burst frequency between the capillary valves largely increases and vice versa for hydrophobic solution.

Based on the aforesaid descriptions, the sequential releasing of fluid is optimized by adjusting the radial location of the valve, valve width, orientation and surface modification of the capillary valves. Therefore, the microfluidic device in accordance with the present invention is useful for various chemical analytical processes.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A microfluidic device comprising:

an annular disk-shaped body having
- a top;
- a center;
- a circumference; and
- a bottom;

multiple reservoirs formed on said top of said body;

multiple channels formed on said top of said body, said channels include
- a main channel formed on said top of said body and extending in a direction from said center to said circumference of said body; and
- at least one branch channel formed on said top of said body and connecting to said reservoirs;

multiple capillary valves, wherein each capillary valve mounted on a corresponding channel and at a distance of lesser than 4 cm to said center of said body, such that differences between burst frequencies of said capillary valves are increased; and a cover mounted on said top of said body and having multiple apertures corresponding to said reservoirs.

2. The microfluidic device of claim 1, wherein
said main channel has
a first end; and
a second end opposite said first end and between said first end and said circumference of said body; and
multiple branch channels connecting to said main channel;
said multiple reservoirs includes
a first reservoir connecting to said first end of said main channel; and
a second reservoir formed between said first reservoir and said circumference of said body and connecting to at least one said branch channel and communicating with said main channel; and
said multiple capillary valves include
a first capillary valve mounted between said first reservoir and said first end of said main channel; and
a second capillary valve mounted between and connecting said branch channel and said second reservoir.

3. The microfluidic device of claim 2, wherein a width of said first capillary valve is smaller than a width of said second capillary valve, whereby difference between said burst frequencies thereof is increased.

4. The microfluidic device of claim 2, wherein
said multiple reservoirs further include
a fifth reservoir connecting to said second end of said main channel; and
a third reservoir mounted between said second reservoir and said fifth reservoir and connecting to said main channel through a corresponding branch channel; and
a fourth reservoir mounted between said third reservoir and said fifth reservoir and connecting to said main channel through another corresponding branch channel; and
said multiple capillary valves further include
a third capillary valve mounted on said corresponding branch channel and between said third reservoir and said main channel; and
a fourth capillary valve mounted on said another corresponding branch channel between said fourth reservoir and said main channel.

5. The microfluidic device of claim 4, wherein a width of said second capillary valve is smaller than a width of said third capillary valve, whereby difference between said burst frequencies thereof is increased.

6. The microfluidic device of claim 5, wherein a width of said third capillary valve is smaller than a width of said fourth capillary valve, whereby difference between said burst frequencies thereof is increased.

7. The microfluidic device of claim 3, wherein said first capillary valve has a hydrophobically modified inner surface.

8. The microfluidic device of claim 5, wherein each of said second capillary valve, said third capillary valve and said fourth capillary valve has a hydrophobically modified inner surface.

9. The microfluidic device of claim 2, which has
an additional branch channel mounted between said main channel and said first reservoir and having
a distal end connecting to said first capillary valve and said main channel; and
a proximal end connecting said distal end and said main channel and not parallel to said main channel.

10. The microfluidic device of claim 7, which has
an additional branch channel mounted between said main channel and said first reservoir and having
a distal end connecting to said first capillary valve and said main channel; and
a proximal end connecting said distal end and said main channel and not parallel to said main channel.

11. The microfluidic device of claim 8, which has
an additional branch channel mounted between said main channel and said first reservoir and having
a distal end connecting to said first capillary valve and said main channel; and
a proximal end connecting said distal end and said main channel and not parallel to said main channel.

12. The microfluidic device of claim 9, wherein said proximal end is vertical to a radial direction of said body.

13. The microfluidic device of claim 10, wherein said proximal end is vertical to a radial direction of said body.

14. The microfluidic device of claim 5, wherein said fifth reservoir is a detection chamber or a waste chamber.

15. The microfluidic device of claim 6, wherein said fifth reservoir is a detection chamber or a waste chamber.

16. The microfluidic device of claim 7, wherein said fifth reservoir is a detection chamber or a waste chamber.

17. The microfluidic device of claim 3, wherein said cover is prepared from the materials selected from the group consisting of:
polycarbonate, poly (methyl methacrylate), polystyrene and cyclic olefin copolymer.

18. The microfluidic device of claim 1, wherein
said body further has
multiple positioning apertures penetrating through said top and the said bottom of said body; and
multiple notches formed on an edge of said body;
said cover further has
multiple positioning holes penetrating through a top and a bottom of said cover and corresponding to said positioning apertures of said body; and
multiple recesses formed on a rim of said cover and corresponding to said notches of said body.

* * * * *